ic Cl.

(12) United States Patent
Chambon et al.

(10) Patent No.: US 8,624,058 B2
(45) Date of Patent: Jan. 7, 2014

(54) PROCESS FOR TRANSFORMATION OF LIGNOCELLULOSIC BIOMASS OR CELLULOSE BY TUNGSTEN-BASED SOLID LEWIS ACIDS

(75) Inventors: Flora Chambon, Bron (FR); Nadine Essayem, Saint Just Chaleyssin (FR); Franck Rataboul, Lyons (FR); Catherine Pinel, Lyons (FR); Amandine Cabiac, Lyons (FR); Emmanuelle Guillon, Vourles (FR)

(73) Assignees: Centre National de la Recherche Scientifique, Paris Cedex (FR); IFP Energies nouvelles, Rueil-Malmaison Cedex (FR)

( * ) Notice: Subject to any disclaimer, the term of this patent is extended or adjusted under 35 U.S.C. 154(b) by 0 days.

(21) Appl. No.: 13/577,988

(22) PCT Filed: Feb. 1, 2011

(86) PCT No.: PCT/FR2011/000062
§ 371 (c)(1),
(2), (4) Date: Oct. 23, 2012

(87) PCT Pub. No.: WO2011/098683
PCT Pub. Date: Aug. 18, 2011

(65) Prior Publication Data
US 2013/0053601 A1    Feb. 28, 2013

(30) Foreign Application Priority Data

Feb. 11, 2010  (FR) ...................................... 10 00573

(51) Int. Cl.
*C07C 51/00*  (2006.01)
*C07C 59/08*  (2006.01)

(52) U.S. Cl.
USPC ........................................... 562/515; 562/589

(58) Field of Classification Search
None
See application file for complete search history.

(56) References Cited

U.S. PATENT DOCUMENTS

2010/0255983 A1* 10/2010 Zhang ........................... 502/178
2011/0313210 A1* 12/2011 Kalnes et al. .................. 568/861

FOREIGN PATENT DOCUMENTS

EP    2 100 871 A1    9/2009
JP    2009-263241 A   11/2009

OTHER PUBLICATIONS

International Search Report of PCT/FR2011/000062 (Apr. 19, 2011).

* cited by examiner

*Primary Examiner* — Karl J Puttlitz
(74) *Attorney, Agent, or Firm* — Millen, White, Zelano & Branigan, P.C.

(57) ABSTRACT

The invention relates to a process for transformation of lignocellulosic biomass or cellulose that uses tungsten-based heterogeneous catalysts that are dispersed on an oxide-based substrate, preferably with a base of oxide(s) of aluminum and/or zirconium and/or titanium and/or niobium. The use of these catalysts makes it possible to obtain directly lactic acid with high selectivity while limiting the production of oligosaccharides and soluble polymers.

20 Claims, No Drawings

PROCESS FOR TRANSFORMATION OF LIGNOCELLULOSIC BIOMASS OR CELLULOSE BY TUNGSTEN-BASED SOLID LEWIS ACIDS

The invention relates to a process for transformation of lignocellulosic biomass or cellulose that uses tungsten-based heterogeneous catalysts that are dispersed on an oxide-based substrate, preferably with a base of oxide(s) of aluminum and/or zirconium and/or titanium and/or niobium. The use of these catalysts makes it possible to obtain directly lactic acid with high selectivity while limiting the production of oligosaccharides and soluble polymers.

PRIOR ART

For several years, there has been a very sharp resurgence of interest for the incorporation of products of renewable origin within the fuel and chemistry branches, in addition to or in place of products of fossil origin. One possible method is the conversion of cellulose, contained in the lignocellulosic biomass, into chemical products or intermediate products, such as lactic acid.

The term lignocellulosic biomass (BLC) or lignocellulose encompasses several products that are present in variable quantities according to the origin thereof: cellulose, hemicellulose and lignin. The hemicellulose and cellulose constitute the carbohydrate portion of the lignocellulose. These are polymers of sugars (pentoses and hexoses). Lignin is a macromolecule that is rich in phenolic units. Lignocellulosic biomass is defined as, for example, the products that are obtained from forestry operations and the sub-products that are obtained from agriculture, such as straw as well as certain dedicated plants with a high agricultural yield.

The production of chemical products from lignocellulosic biomass makes it possible both to reduce the energy dependency relative to petroleum and to protect the environment through reducing greenhouse gas emissions without using resources designed for food uses.

The direct transformation of lignocellulosic biomass or cellulose into chemical products or intermediate products, such as lactic acid, is a particularly advantageous method. Direct transformation is defined as the cellulose-lactic acid transformation without passing through the glucose intermediate product.

Lactic acid is a carboxylic acid; its chemical formula is $C_3H_6O_3$ and its structure is reflected in its systematic name, 2-hydroxy-propanoic acid. Since it has an asymetrical carbon, there are two enantiomers of lactic acid. The applications of the lactic acid are primarily those of its polymer PLA (polylactic acid) as a food preservative but also as biodegradable polymers, pesticides and herbicides.

The production of lactic acid can be done by chemical methods or by biological methods. The chemical methods for the production of lactic acid that are known to one skilled in the art are done via the transformation of petrochemical intermediate products such as the hydrolysis of lactonitrile or the hydration of propionic acid. Lactic acid can also be produced by fermentation of polysaccharides, which can be obtained from biomass, for example obtained from grains such as wheat or corn. The patent application EP 1953234 relates to a process for the production for lactic acid by fermentation of a sugar cane extract, by means of a microorganism belonging to the genera *Bacillus* or *Sporolactobacillus*.

The upgrading of the lignocellulosic biomass or the cellulose that is contained in the biomass in heterogeneous catalysis is described in the literature. For example, the hydrolysis of the cellulose into glucose or sorbitol in an aqueous medium on heterogeneous metallic catalysts is described in the patent application EP 2011569. Rinaldi et al. describe the depolymerization of the cellulose in an ionic liquid medium in the presence of Brønsted acid catalysts (Angew. [Applied] Chem. Int. Ed., 2008, 47, 8047-8050). Zeng et al. describe the conversion of glucose into lactic acid, 5-(hydroxymethyl) furfural and levulinic acid in the presence of basic catalysts of Al/Zr mixed oxide types (Catal. Lett. (2009) 133: 221-226).

Also, the production of lactic acid by treatment of cellulose/lignocellulose under hydrothermal conditions in the presence of basic homogeneous catalysts is known. By basic homogeneous catalysis, Fangmin Jin and Heiji Einomoto (J. Mater. Sci. (2008) 43: 2463-2471) record a yield of 27% lactic acid in the presence of $Ca(OH)_2$ at a temperature of 300° C. in less than 5 minutes of reaction. Kong et al. (J. Chem. Technol. Biotechnol. 83: 383-388 (2008)) describe a hydrothermal process for the production of lactic acid from biomass in a subcritical water medium in the presence of cations of transition metals Zn(II), Ni(II), Co(II), and Cr(III). WO 03/035582 describes the hydrogenolysis of sorbitol at 200° C. by using (Ni, Re)/C catalysts that leads to lactic acid yields of 5% and 30% of diols (ethylene glycol and propylene glycol). Shimizu et al. (Green Chem., 2009, 11, 1627-1632) showed the essential role of Brønsted acidity on the hydrolysis of cellulose into glucose. Zhang et al. (Angew. Chem. Int. Ed. 2008, 47, 8510-8513) studied the transformation of cellulose into ethylene glycol and propylene glycol on tungsten carbide/activated carbon catalysts with nickel as a promoter (T=245° C., p=6 MPa, $H_2$, water).

There is no process that makes possible a direct transformation, i.e., without passing through the intermediary of glucose, cellulose, or, more broadly, lignocellulosic biomass into lactic acid by means of heterogeneous catalysts. The applicant discovered a process for direct transformation of cellulose, present in the lignocellulosic biomass, into lactic acid, implementing tungsten-based heterogeneous catalysts dispersed on an oxide substrate. In addition, this process makes it possible to obtain a high yield of lactic acid.

OBJECT OF THE INVENTION

The invention consists of a process for transformation of the lignocellulosic biomass or cellulose into lactic acid in the presence of water, using tungsten-based heterogeneous catalysts that are dispersed on an oxide substrate. The process makes it possible to obtain high conversions of the reagent and important selectivities, in particular high yields of lactic acid, while limiting the formation of oligosaccharides or water-soluble polymers. These conversions and selectivities are obtained only under hydrothermal conditions (presence of water) and in the presence of tungsten-based catalysts that have Lewis-type acid properties. Actually, the solid catalysts for the most part having a Brønsted acidity promote the production of soluble oligosaccharides and/or soluble polymers, showing a lower selectivity in desired chemical intermediate products.

DETAILED DESCRIPTION OF THE INVENTION

The invention relates to a process for transformation of lignocellulosic biomass or lactic acid cellulose comprising putting the lignocellulosic biomass or the cellulose in the presence of water into contact with a tungsten-based heterogeneous catalyst that is dispersed on an oxide-based substrate, preferably a substrate with a base of oxide(s) of aluminum and/or zirconium and/or titanium and/or niobium, whereby said catalyst has Lewis-type acid sites. The content of Lewis-type acid sites of the catalyst is preferably greater than 50%. The use of these catalysts makes it possible to obtain the lactic acid directly in high selectivity while limiting the production of oligosaccharides and soluble polymers.

The Feedstock

The lignocellulosic biomass essentially consists of three natural components that are present in variable amounts according to the origin thereof: cellulose, hemicellulose, and lignin.

The cellulose $(C_6H_{10}O_5)_n$ shows the major portion (50-60%) of the composition of the lignocellulosic biomass. The cellulose is a semi-crystalline linear homopolymer of glucose connected by the bonds β. The cellulose is insoluble in water at ambient temperature and pressure.

Hemicellulose is the carbohydrate that is second in quantity after cellulose and constitutes 20 to 40% by weight of the lignocellulosic biomass. Contrary to cellulose, this polymer consists for the most part of monomers of pentoses (cyclic compounds with five atoms) and hexoses (cyclic compounds with 6 atoms). Hemicellulose is an amorphous heteropolymer with a degree of polymerization that is less than that of cellulose (30-100) and that is generally water-soluble.

Lignin is an amorphous macromolecule that is present in the lignocellulosic compounds in variable proportions according to the origin of the material (straw ~15%, wood: 20-26%). Its function is mechanical reinforcement, hydrophobization, and support of plants. This macromolecule that is rich in phenolic units can be described as a resultant of the combination of three monomer units of the propyl-methoxyphenol type. Its molar mass varies from 5,000 g/mol to 10,000 g/mol for hardwoods and reaches 20,000 g/mol for softwoods.

The lignocellulosic raw material can consist of wood or plant waste. Other nonlimiting examples of lignocellulosic biomass material are waste from agricultural operations (straw, grasses, stems, pits, shells, . . . ), waste from forestry operations (initial cutting products, bark, sawdust, chips, scraps, . . . ), products from forestry operations, dedicated crops (short-rotation shrubs), waste from the food-processing industry (waste from the industry of cotton, bamboo, sisal, banana, corn, switchgrass, alfalfa, coconut, bagasse, . . . ), household organic waste, waste from wood transformation plants, scrap wood from construction, and paper, which may or may not be recycled.

The feedstock that is used in the process according to the invention is lignocellulosic biomass or cellulose. The cellulose that is used may be crystalline or amorphous.

The lignocellulosic biomass feedstock can be used in its raw form, i.e., is made up in its entirety of these three cellulose, hemicellulose and lignin components. The raw biomass generally comes in the form of fibrous residues or powder. In general, it is ground to allow the transport of the latter (shredding).

The lignocellulosic biomass feedstock can also be used in its pretreated form, i.e., in a form that contains at least one cellulosic portion after extraction of lignin and/or hemicellulose.

The biomass preferably undergoes a pretreatment so as to increase the reactivity and the accessibility of cellulose within the biomass before its transformation. These pretreatments are of a mechanical, thermochemical, thermal-mechanical-chemical and/or biochemical nature, and bring about the decrystallization of cellulose, the solubilization of hemicellulose and/or lignin, or the partial hydrolysis of hemicellulose following the treatment.

The mechanical treatments go beyond simple shredding because they modify the chemical structure of the components. They improve the accessibility and the reactivity of the cellulose by its decrystallization and by the increase of the exchange surface area. The mechanical treatments include the reduction of the size of fibers or elementary particles, for example by chipping the biomass with a cutter, by grinding the biomass (adjustment of the grain size), destructuring chips on a press, or grinding by chip abrasion, after preheating. The mechanical treatments can be performed in decentralized mode close to where the biomass is produced or in a centralized mode that directly feeds the transformation.

The thermochemical treatments include the baking of the biomass at high temperature (150-170° C.) in a dilute acid medium (primarily sulfuric acid, but also phosphoric acid, acetic acid, or formic acid), in an alkaline medium (soda, sulfites, lime, . . . ) or in an oxidizing medium (wet oxidation with air or oxygen; peroxide in an alkaline medium; peracetic acid). The other thermochemical treatments include treatments with solvents (hot ethanol) or roasting that can be defined as pyrolysis at moderate temperature and with a controlled dwell time because it is accompanied by partial destruction of the lignocellulosic material. The known technologies for roasting are, for example, the rotary kiln, moving bed, fluidized bed, heated endless screw, and the contact with metal balls that provide heat. These technologies can optionally use a gas that circulates in co-current or counter-current such as nitrogen or any other inert gas under the conditions of the reaction.

The thermal-mechanical-chemical treatments include vapor treatments (vapor explosion also called flash hydrolysis or "steam explosion"), the AFEX (ammonia fiber explosion) treatment with ammonia, or two-screw extrusion with various chemical reagents.

The pretreatment makes it possible to prepare the lignocellulosic biomass by separating the carbohydrate part of the lignin and by adjusting the size of the biomass particles that are to be treated. The size of the biomass particles after pretreatment is generally less than 5 mm, preferably less than 500 microns.

The Catalyst

The catalysts that are used for the transformation of the lignocellulosic biomass or cellulose are based on tungsten oxide that is dispersed on the surface of an oxide substrate, preferably a substrate of oxide(s) of aluminum and/or zirconium and/or titanium and/or niobium, whereby said catalysts have Lewis-type acid sites.

In a general manner, the acidity of the catalyst is the resultant of two combined types of acidity: Lewis acidity, characterized by the presence of an electron gap on an atom, and Brønsted acidity, characterized by a capability of giving up a proton. The nature of the acid sites can be characterized by adsorption of pyridine followed by IR spectroscopy in accordance with the method that is described in [M. Guisnet, P. Ayrault, C. Coutanceau, M. F. Alvarez, J. Datka, *J. Chem. Soc., Faraday Trans.* 93, 1661 (1997)].

The solids according to the invention are characterized by superficial acidic properties that are for the most part of the Lewis acid type, preferably greater than 50%. The Lewis-type acid sites are associated with the presence of tungsten radicals that are coordinatively unsaturated but also with radicals that are characteristic of the substrate: $Al^{3+}$, $Zr^{4+}$, $Ti^{4+}$, and $Nb^{5+}$. It is known that the coordination of the surface tungsten radicals (tetrahedral/octahedral) depend on their dispersion, the W content, the nature of the precursors, and the heat treatments.

The ZrW-type catalysts, combined or not with a metal phase, are described for being active in many applications such as the hydroisomerization of paraffins (U.S. Pat. No. 6,124,232) or the dimerization of olefins (U.S. Pat. No. 5,453, 556). Zirconium tungstate is commonly prepared by impregnation or co-precipitation: the tungsten oxides that are supported on zirconia were described for the first time by Hino and Arata (J. Chem. Soc., Chem. Commun., 1148 (1979)). This solid is obtained by impregnation of zirconia by ammonium metatungstate, followed by decomposition in air at 800-850° C. The U.S. Pat. No. 5,510,309 discloses a solid that is obtained by co-precipitation of ammonium metatungstate and $ZrOCl_2$, followed by calcination at a temperature of greater than 700° C.

Although the tungsten/Zr and/or Al and/or Ti and/or Nb catalysts are known, they have never been applied in the conversion of lignocellulosic materials or cellulose in the presence of water and more particularly for selectively producing important chemical intermediate products such as lactic acid.

The catalysts that are used in the process according to this invention can be synthesized by ion exchange, by impregnation, or by co-precipitation followed by a heat treatment. The solids that are obtained have the advantages of being mesoporous and stable, thermally and under hydrothermal conditions.

The catalysts that are used in this invention can be in the form of powder, extrudates, balls or pellets.

The oxide substrates are preferably selected from among the oxides/hydroxides of aluminum and/or zirconium and/or titanium and/or niobium.

The tungsten content is between 2 and 30% by weight, preferably between 10 and 20% by weight, or else preferably between 2 to 20% by weight, with the percentages being expressed in terms of % by weight of metal relative to the total mass of catalyst.

The tungsten precursors are selected from among tungstic acid, peroxotungstic acid, ammonium metatungstate, or tungsten-based isopolyanions or heteropolyanions. The ammonium metatungstate is the usual precursor. The use of tungstic acid in solution in hydrogen peroxide is preferred because by this method, the formation of monomeric tungsten radicals in solution is promoted, said radicals that are exchangeable at acidic pH with substrates based on Zr, Ti, Al and/or Nb according to the invention WO 2004/004893.

The preferred preparation method consists of an anion exchange between a tungstic acid solution in hydrogen peroxide and the hydroxide of zirconium and/or titanium and/or aluminum and/or niobium, followed by a calcination according to US 2006/0091045.

Transformation Process

The process for transformation of the lignocellulosic biomass or cellulose according to the invention comprises the reaction in a water-containing medium in the presence of the catalytic composition according to the invention.

Water-containing medium refers to the conventional liquid media (such as, for example, ethanol or water) and the non-conventional media, such as the ionic liquids or the supercritical media of liquid-type density.

The content by mass of water in the medium is generally greater than 1%. The medium can also consist entirely of water. Preferably, the medium is water.

This process can be carried out in the presence of a gas that is selected from among air, a neutral gas ($N_2$, He, Ar . . . ) or a reducing gas such as hydrogen. Preferably, hydrogen is used because a better conversion of cellulose and a better yield of lactic acid are observed.

The process is carried out at temperatures of between 160° C. and 250° C., preferably between 175 and 250° C., and at a pressure of between 0.5 and 20 MPa, preferably between 2 and 10 MPa.

In general, the reaction can be performed according to different embodiments. Thus, the reaction can be implemented intermittently or continuously, for example in a fixed bed. It is possible to operate with a closed or half-open reactor.

The catalyst is introduced into the process at a rate of a quantity that corresponds to the biomass/catalyst mass ratio of between 1 and 1,000, preferably between 1 and 500, preferably between 1 and 100, preferably between 1 and 50, and even preferably between 1 and 25.

The biomass is introduced into the process at a rate of a quantity that corresponds to a mass ratio (water-containing medium)/biomass of between 1 and 1,000, preferably between 1 and 500, and even preferably between 5 and 100. The dilution rate of the biomass is therefore between 1:1 and 1:1,000, preferably between 1:1 and 1:500, and even preferably between 1:5 and 1:100.

If a continuous process is selected, the mass speed per hour (mass/catalyst mass feedstock flow rate) is between 0.01 and 5 $h^{-1}$, preferably between 0.02 and 2 $h^1$.

The Products that are Obtained and Their Mode of Analysis

After the reaction, the reaction medium is sampled and centrifuged. The reaction liquid is next analyzed by liquid chromatography under high pressure (HPLC) by using refractometry for determining the content of conversion products of the aqueous solution.

The products of the reaction are soluble in water. They consist of monosaccharides and their derivatives, oligosaccharides, but also soluble polymers that are formed by successive combinations of the derivatives of monosaccharides.

Monosaccharides refers to the simple sugars (hexoses, pentoses) that are produced by complete depolymerization of the cellulose and/or hemicellulose, in particular glucose, mannose, xylose, fructose, . . . .

Monosaccharide derivatives refer to the products that can be obtained by dehydration, isomerization, reduction or oxidation:

Alcohol sugars, alcohols and polyols: in particular, sorbitol, xylitol, glycerol, ethylene glycol, propylene glycol, ethanol, Me-butane diols . . . , Ketones, hexane-diones: 2,5-hexanedione . . . , Carboxylic acids and their esters, lactones: formic acid, levulinic acid, alkyl levulinates, lactic acid, alkyl lactic acid, glutaric acid, alkyl glutarates, 3-hydroxypropanoic acid, 3-hydroxybutyrolactone, γ-butyrolactone, Cyclic ethers: THF, Me-THF, dicarboxylic acid furan, 5-(hydroxymethyl)furfural.

Oligosaccharides refer to a carbohydrate that has as its composition $(C_6H_{10}O_5)_n$, where n is greater than 1, obtained by partial hydrolysis of cellulose, hemicellulose, or starch.

Soluble polymers refer to all of the products that are obtained from condensation between monosaccharides, oligosaccharides and/or derivatives of monosaccharides.

The quantity of water-soluble reaction products (monosaccharides and derivatives, oligosaccharides, soluble polymers) is determined by the COT [TOC] (Total Organic Carbon) analysis that consists in the measurement of carbon in solution. The quantity of monosaccharides and their derivatives is determined by HPLC analyses.

The conversion (equivalent to % of solubilization) of the biomass or cellulose is calculated according to the following equation:

$$C=100*C_{solubilized}/C_{initial} \quad 5$$

in which $C_{solubilized}$ represents the quantity of solubilized carbon that is analyzed by TOC (mg), and $C_{initial}$ represents the quantity of carbon at the beginning of the reaction that is contained in the biomass or solid cellulose.

The molar yields of glucose derivatives are calculated by means of HPLC analysis. Each compound is corrected by the carbon atom number contained in the glucose unit.

The molar yields of a derivative i are calculated as follows:

$$Rdt_i=100*(nC_{Pi}/6)*(P_i/Glu_o)$$

where $nC_{Pi}$ represents the number of carbon atoms of the derivative i, Pi represents the number of moles of the product $P_i$, and $Glu_0$ represents the number of moles of glucose units contained in the biomass or cellulose at the beginning of the reaction.

The formations of oligosaccharides and soluble polymers correspond to a loss of carbon. This loss of carbon is deduced from TOC analyses and HPLC. The yield of oligosaccharides and soluble polymers is calculated according to the following equation:

$$Rdt_{olig}=C-\Sigma rdt_i$$

where C represents the conversion of the cellulose and $\Sigma rdt_i$ represents the sum of molar yields of all of the monosaccharides and their derivatives that are analyzed by HPLC.

EXAMPLES

Preparation of Two Catalysts According to the Invention

Example 1

Preparation of a Zirconium Tungstate

Zirconium hydroxide ($Zr(OH)_4$) is prepared in a first stage. It is prepared by precipitation at a constant pH of 9 from a 0.4 M solution of zirconyl chloride ($ZrOCl_2$, $8H_2O$) and a 1.8 M ammonia solution. The suspension that is obtained is stirred for 20 minutes. The precipitate is separated by centrifuging and washed several times with deionized water so as to eliminate chloride ions. The solid that is obtained is next dried at 110° C. for 24 hours.

The zirconium tungstate was synthesized in accordance with the teaching of the patent US 2006/0091045. This dried zirconium hydroxide (10 g) is next subjected to an ion exchange for 15 minutes by using a 0.25 M tungstic acid solution in 30% hydrogen peroxide (150 ml). After this exchange, the solid is filtered and then dried at 80° C. for 24 hours. Next, the solid that is obtained is calcined under a flow of dry air at the temperature of 700° C. for 3 hours.

At the end of these treatments, the thus obtained zirconium tungstate contains 11.7% by weight of tungsten. The nature of the acid sites of this catalyst has been characterized by pyridine adsorption followed by IR spectroscopy in accordance with the method that is described in [M. Guisnet, P. Ayrault, C. Coutanceau, M. F. Alvarez, J. Datka, *J. Chem. Soc., Faraday Trans.* 93, 1661 (1997)]. More than 65% of the acid sites of this tungsten-based catalytic formulation are Lewis-type acid sites.

Example 2

Preparation of an Aluminum Tungstate (18% by Weight of Tungsten)

The raw material that is used is aluminum hydroxide (boehmite). This aluminum hydroxide (10 g) is subjected to an anion exchange using tungstic acid in solution (0.25 M) in 30% hydrogen peroxide (150 ml). The exchange lasts for 15 minutes at ambient temperature. After this exchange, the solid is filtered and then dried at 80° C. for 24 hours.

Next, the solid that is obtained is calcined under a flow of dry air at the temperature of 700° C. for 3 hours.

At the end of these treatments, the thus obtained aluminum tungstate contains 18% by weight of tungsten.

The nature of the acid sites of this catalyst was characterized by the method that is described in Example 1. More than 90% of the acid sites of this tungsten-based catalytic formulation are Lewis-type acid sites.

Preparation of a Catalyst that is not in Accordance with the Invention (Brønsted Acid)

Example 3

Preparation of a Cesium Acid Salt from 12-Tungstophosphoric Acid $H_3PW_{12}O_{40}$ The raw material that is used is the hydrated 12-tungstophosphoric acid $H_3PW_{12}O_{40} \cdot 21H_2O$ and cesium chloride. The cesium acid salt $Cs_2HPW_{12}O_{40}$ is prepared by precipitation by adding an aqueous solution of cesium chloride (5 M) to a solution of $H_3PW_{12}O_{40}$ in water (0.5 M) at a rate of quantities corresponding to a $CsCl/H_3PW_{12}O_{40}$ molar ratio of 2. The aqueous suspension is allowed to stir for 12 hours at ambient temperature. The precipitated solid is next separated by centrifuging and washed three times with deionized water between each centrifuging. The solid that is obtained is dried by freeze-drying.

The nature of the acid sites of this catalyst was characterized by the method that is described in Example 1. 100% of the acid sites of this tungsten-based catalytic formulation are Brønsted-type acid sites.

Example 4

Transformation of Cellulose that Uses Catalysts According to the Invention and Catalysts that are not in Accordance with the Invention This invention relates to the conversion of the cellulose from different catalysts for the production of lactic acid.

65 ml of water, 1.6 g of Avicel® cellulose (70% crystallinity) and 0.68 g of catalyst of Examples 1 to 3 are introduced into a 100 ml autoclave. The cellulose/catalyst mass ratio is 2.35. It is heated to 190° C., and 5 MPa of $H_2$ is injected. The total pressure then reaches 6 MPa. After 24 hours of reaction, the reaction medium is sampled and centrifuged. The reaction liquid is next analyzed by liquid chromatography under high pressure (HPLC) by using refractometry for determining the content of conversion products of the aqueous solution according to the equations that are described above.

The transformation reaction was also carried out with the non-tungstate oxide substrates $Al_2O_3$ or $ZrO_2$.

The results that are obtained are referenced in Table 1.

TABLE 1

Conversion of Cellulose and Yields of Lactic Acid and Oligosaccharides and Soluble Polymers that Use Different Catalysts.

| Catalyst | Cellulose Conversion (%) | Molar Yield of Lactic Acid (%) | Molar Yields of Oligosaccharides and Soluble Polymers (%) |
|---|---|---|---|
| $Cs_2HPW_{12}O_{40}$ (Example 3, Not in Accordance) | 32 | 5 | 15 |
| $Al_2O_3$ (Not in Accordance) | 35 | 3 | 7 |
| AlW (18% by Weight of W) (Example 2) | 55 | 28 | 7 |
| AlW (5% by Weight of W) (Example 5) | 35 | 19 | 0 |
| $ZrO_2$ (Not in Accordance) | 43 | 2 | 19 |
| ZrW (Example 1) | 67 | 14 | 0 |

In a general manner, it is found that for the catalyst $Cs_2HPW_{12}O_{40}$, the quantity of lactic acid that is formed represents 5 mol % of the quantity of initial cellulose, with 15 mol % of oligosaccharides and soluble polymers. The conversion is 32%.

It thus is found that for the catalyst AlW at 18% by weight of W, the quantity of lactic acid that is formed represents 28 mol % of the quantity of initial cellulose, with 7 mol % of oligosaccharides and soluble polymers. The conversion is 55%.

It is found that for the catalyst ZrW, the quantity of lactic acid that is formed represents 14 mol % of the quantity of initial cellulose, without formation of oligosaccharide and soluble polymers. The conversion is 67%.

The influence of the tungsten compound in the production of lactic acid is shown in the comparison of tests of the tungstate catalysts with substrates of oxides without tungsten ($Al_2O_3$ and $ZrO_2$). A molar yield of lactic acid that is 9 times (7 times) larger is observed in the presence of tungsten in the case of aluminum (zirconium). This is due to the presence of Lewis-type acid sites on these catalysts.

Preparation of a Catalyst According to the Invention that has a Low Tungsten Content Example 5

Preparation of an Aluminum Tungstate (5% by Weight of Tungsten)

The raw material that is used is aluminum hydroxide (boehmite). This aluminum hydroxide (10 g) is subjected to an anion exchange with tungstic acid in solution (0.12 M) in 30% hydrogen peroxide (150 ml). The exchange lasts for 15 minutes at ambient temperature. After this exchange, the solid is filtered and then dried at 80° C. for 24 hours.

Next, the solid that is obtained is calcined under a flow of dry air at the temperature of 700° C. for 3 hours.

At the end of these treatments, the thus obtained aluminum tungstate contains 5% by weight of tungsten.

The nature of the acid sites of this catalyst was characterized by the method that is described in Example 1. More than 90% of the acid sites of this tungsten-based catalytic formulation are Lewis-type acid sites.

The results that are obtained are referenced in Table 1.

Thus, for the catalyst AlW with 5% by weight of W, it is found that the quantity of lactic acid that is formed represents 19 mol % of the quantity of initial cellulose, without formation of oligosaccharides and soluble polymers. The conversion is 35%.

By comparing these results with the results obtained with the catalyst AlW at 18% by weight of W, it is noted that a lower content of tungstate compound makes it possible to obtain a respectable conversion, a good selectivity of lactic acid without formation of oligosaccharides and soluble polymers. It is therefore possible to use a catalyst that has a lower cost.

Example 6

Transformation of Cellulose that Uses the Catalyst AlW with Different Biomass/Catalyst Mass Ratios Example 4 is repeated with the catalyst AlW with 18% by weight of W of Example 2 by using a cellulose/AlW mass ratio of 23.5.

65 ml of water, 1.6 g of Avicel® cellulose (70% crystallinity), and 0.068 g of catalyst AlW are introduced into a 100 ml autoclave. It is heated to 190° C., and 5 MPa of $H_2$ is injected. The total pressure then reaches 6 MPa. After 24 hours of reaction, the reaction medium is sampled and centrifuged. The reaction liquid is next analyzed by liquid chromatography under high pressure (HPLC) by using refractometry for determining the content of conversion products of the aqueous solution according to the equations described above.

The results that are obtained are referenced in Table 2.

TABLE 2

Conversion of Cellulose and Yields of Lactic Acid and Oligosaccharides and Soluble Polymers that Use the Catalyst AlW with 18% by Weight of W at Different Biomass/Catalyst Mass Ratios

| | Catalyst | Cellulose/ Catalyst Mass Ratio | Cellulose Conversion (%) | Molar Yield of Lactic Acid (%) | Molar Yields of Oligosaccharides and Soluble Polymers (%) |
|---|---|---|---|---|---|
| Ex. 4 | AlW (Ex. 2) | 2.35 | 55 | 28 | 7 |
| Ex. 6 | AlW (Ex. 2) | 23.5 | 40 | 17 | 1 |

It thus is found that for a cellulose/AlW ratio of 23.5, the quantity of lactic acid that is formed represents 17 mol % of the quantity of initial cellulose, with only 1 mol % of oligosaccharides and soluble polymers. The conversion is 40%.

Despite the smaller quantity of catalyst, a higher cellulose/catalyst ratio makes it possible to obtain a respectable conversion and good selectivity in terms of lactic acid with very little formation of oligosaccharides and soluble polymers.

Thus, these examples demonstrate the production of high-yield lactic acid by direct transformation of cellulose via tungsten-based heterogeneous catalysts while limiting the formation of oligosaccharides and soluble polymers.

The invention claimed is:

1. A process for transformation of lignocellulosic biomass into lactic acid, comprising contacting the lignocellulosic biomass or cellulose in the presence of water with a heterogeneous catalyst having a tungsten content of 2 to 20% by weight, expressed in % by weight of metal relative to the total mass of the catalyst, said catalyst being dispersed on an oxide-based substrate, and said catalyst having greater than 50% Lewis-type acid sites.

2. The process according to claim 1, wherein said oxide-based substrate is an oxide(s) of aluminum and/or zirconium and/or titanium and/or niobium.

3. The process according to claim 1, wherein the tungsten content of the catalyst is between 10 to 20% by weight expressed in % by weight of metal relative to the total mass of catalyst.

4. The process according to claim 1, wherein the transformation is implemented in a water-containing medium.

5. The process according to claim 4, wherein the content by mass of water in the medium is greater than 1%.

6. The process according to claim 4, wherein said medium is water.

7. The process according to claim 1, wherein the transformation is carried out at a temperature of between 160 and 250° C., and at a pressure of between 0.5 and 20 MPa.

8. The process according to claim 1, wherein the transformation is carried out in the presence of a gas that is air, a neutral gas or a reducing gas.

9. The process according to claim 1, wherein the catalyst is introduced at a rate of a quantity that corresponds to a biomass/catalyst mass ratio of between 1 and 1,000.

10. The process according to claim 1, wherein the biomass or cellulose is introduced at a rate of a quantity that corresponds to a (water-containing medium)/biomass mass ratio of between 1 and 1,000.

11. The process according to claim 1, wherein the tungsten-based heterogeneous catalyst is prepared by ion exchange, impregnation or by co-precipitation, followed by a heat treatment.

12. The process according to claim 11, wherein the tungsten precursor of the catalyst is tungstic acid, peroxotungstic acid, ammonium metatungstate, or tungsten-based isopolyanions or heteropolyanions.

13. The process according to claim 1, wherein the tungsten-based heterogeneous catalyst is prepared by an anion exchange between a tungstic acid solution in hydrogen peroxide and hydroxide of Zr and/or Ti and/or Al and/or Nb, followed by calcination.

14. The process according to claim 1, wherein before its transformation, the lignocellulosic biomass undergoes a stage of mechanical, thermochemical, thermal-mechanical-chemical or biochemical pretreatment.

15. The process according to claim 14, wherein the size of the biomass particles after pretreatment is less than 5 mm.

16. The process according to claim 1, wherein the transformation is implemented in a water-containing medium, with said medium being a liquid medium that is ethanol, water, an ionic liquid or a supercritical medium of liquid-type density.

17. The process according to claim 1, wherein the transformation is carried out at a temperature of between 175 and 250° C., and at a pressure of between 2 and 10 MPa.

18. The process according to claim 1, wherein the transformation is carried out in the presence of a gas that is air, a neutral gas or a reducing gas hydrogen.

19. The process according to claim 1, wherein the catalyst is introduced at a rate of a quantity that corresponds to a biomass/catalyst mass ratio of between 1 and 50.

20. The process according to claim 1, wherein the biomass or cellulose is introduced at a rate of a quantity that corresponds to a (water-containing medium)/biomass mass ratio of between 5 and 100.

\* \* \* \* \*